United States Patent [19]

Tyers

[11] Patent Number: 4,985,437

[45] Date of Patent: Jan. 15, 1991

[54] MEDICAMENTS
[75] Inventor: Michael B. Tyers, Ware, England
[73] Assignee: Glaxo Group Limited, England
[21] Appl. No.: 133,885
[22] Filed: Dec. 16, 1987
[30] Foreign Application Priority Data

| Dec. 17, 1986 | [GB] | United Kingdom | 8630077 |
| Dec. 17, 1986 | [GB] | United Kingdom | 8630076 |
| Dec. 17, 1986 | [GB] | United Kingdom | 8630074 |
| Mar. 25, 1987 | [GB] | United Kingdom | 8707175 |

[51] Int. Cl.$^5$ .............................................. A61K 31/46
[52] U.S. Cl. ........................................................ 514/304
[58] Field of Search .......................................... 514/304

[56] References Cited

U.S. PATENT DOCUMENTS

| 4,624,961 | 11/1986 | Welstead, Jr. |  |
| 4,721,720 | 1/1988 | Wootton et al. |  |
| 4,789,673 | 12/1988 | Donatsch et al. | 514/304 |
| 4,803,199 | 2/1989 | Donatsch et al. | 514/304 |
| 4,826,838 | 5/1989 | Richardson et al. | 514/304 |
| 4,851,407 | 7/1989 | Wootton et al. | 514/304 |

FOREIGN PATENT DOCUMENTS

| 0189002 | 7/1986 | European Pat. Off. |
| 0190920 | 8/1986 | European Pat. Off. |
| 2125398A | 3/1984 | United Kingdom. |
| 2193633A | 2/1988 | United Kingdom. |

OTHER PUBLICATIONS

Altman et al., *Psychopharmacology*, 90, 24–27 (1986).
Essman, *Advances in Biochemical Psychopharmacology*, 11, 265–274 (1974).

Primary Examiner—Olik Chaudhuri
Assistant Examiner—Jerry D. Johnson
Attorney, Agent, or Firm—Bacon & Thomas

[57] ABSTRACT

The invention relates to the use of certain compounds which act as antagonists of 5-hydroxytryptamine (5-HT) at 5-HT$_3$ receptors for the treatment of cognitive disorders such as attentional and memory deficits and dementia states.

5 Claims, No Drawings

MEDICAMENTS

This invention relates to a new medical use for certain chemical compounds and pharmaceutical compositions containing them. In particular it relates to the use in the treatment of dementia and other cognitive disorders of certain compounds which act as antagonists of 5-hydroxytryptamine (5-HT) at receptors known in the art as 5-HT$_3$, 5-HT'M' or 5-HT 'M'-like' receptors. Such receptors have been described for example by Fozard et al., Eur. J. Pharmacol., 1979, 59, 195–210; Ireland, Straughan and Tyers, Br. J. Pharmacol., 1982, 75, 16P; Humphrey, Neuropharm., 1984, 23, 1503–1570; Richardson et al., Nature, 1985, 316, 126–131; and Bradley et al., Neuropharm., 1986, 25, 563–576. Receptors of this type are now designated as 5-HT$_3$ receptors.

5-HT receptors of this type are located, for example, on the terminals of afferent sensory neurones, in the isolated quinea-pig ileum preparation and are also present in the central nervous system. Compounds which act as antagonists of 5-HT at 5-HT$_3$ receptors may be identified using standard tests, for example, in vitro by measuring their inhibition of the depolarising effect of 5-HT on the rat or rabbit isolated vagus nerve, or the tachycardia produced by 5-HT in the rabbit isolated heart or the contraction produced by 5-HT in the quinea-pig isolated ileum, or in vivo by measuring their effect on the Von Bezold-Jarisch reflex (induced by 5-HT) as described, for example, in the above-mentioned references.

A variety of compounds which act as antagonists of 5-HT at 5-HT$_3$ receptors have been described in the art. Such compounds have been disclosed inter alia in published U.K. Patent Applications Nos. 2100259, 2125398, 2131420, 2132189, 2145416, 2152049, 2153821 and 2169292, published European Patent Applications Nos. 111608, 116255, 158265, 191562, 200444, 210840, 214772, 219193, 221702, 226267, 227215, 230718, 235878 and 242973, and published Australian Patent Application No. 87/67121. The compounds disclosed in published European Patent Application Nos. 13138, 67615, and 94742 have also been described as antagonists of 5-HT at 5-HT$_3$ receptors, in published European Patent Applications Nos. 215545 and 220011.

The compounds disclosed in these specifications have been described as being of use in a variety of conditions, including migraine.

We have now found that compounds which are disclosed in the above specifications and act as 5-HT antagonists at 5-HT$_3$ receptors are useful in the treatment of cognitive disorders such as attentional and memory deficits and dementia states. These types of condition occur in, for example, senile dementia of the Alzheimers type, ageing, cerebrovascular deficiency and Parkinson's disease.

Accordingly the invention provides a method of treatment of a subject, in particular a human subject, suffering from dementia or another cognitive disorder, which comprises administering to the subject an effective amount of a compound selected from compounds of formulae (I) to (VIII) as defined hereinafter or a physiologically acceptable salt or solvate thereof.

The effectiveness of the compounds for use according to the present invention in the treatment of cognitive disorders may be demonstrated in rats in the spontaneous alternation test and in marmosets given learning tasks in the Wisconsin General Test Apparatus.

References in this specification to treatment include prophylactic treatment as well as the acute alleviation of symptoms.

Particular compounds for use in the present invention are those which act as antagonists of 5-HT at 5-HT$_3$ receptors and are disclosed in published U.K. Patent Specifications Nos. 2100259, 2131420, 2132189, 2145416, 2152049, 2153821 and 2169292, published European Patent Specifications Nos. 13138, 67615, 111608, 116255, 158265, 191562, 200444, 210840, 219193, 221702, 226267, 227215, 230718, 235878 and 242973, published Australian Patent Application No. 87/67121, and compounds of formula (I) as defined hereinafter. Compounds of formula (I) are described in U.K. Patent Specification No. 2125398.

Preferred compounds for use according to the invention are those compounds which act as antagonists of 5-HT at 5-HT$_3$ receptors described in published U.K. Patent Specification Nos. 2100259, 2132189, 2152049 and 2153821, published European Patent Specification Nos. 13138, 116255, 200444, 221702, 226267, 235878 and 242973, published Australian Patent Application No. 87/67121, and compounds of formula (I) as defined hereinafter.

Particularly preferred compounds for use according to the present invention are those described in published U.K. Patent Specification No. 2100259, published European Patent Specification Nos. 200444 and 242973, and compounds of formula (I) as defined hereinafter.

A preferred group of compounds for use according to the invention, described in U.K. Specification No. 2125398, may be represented by the general formula (I):

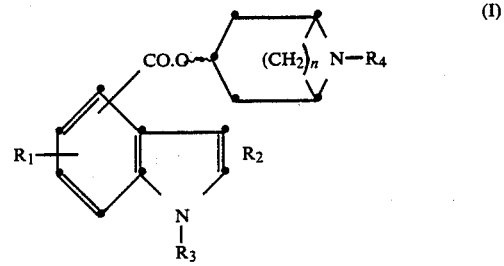

wherein $R_1$ and $R_2$ independently represent hydrogen, halogen, $C_{1-4}$ alkyl, $C_{1-4}$ alkoxy, hydroxy, amino, $C_{1-4}$ alkylamino, di($C_{1-4}$)alkylamino, mercapto or $C_{1-4}$ alkylthio;

$R_3$ represents hydrogen, $C_{1-4}$ alkyl, $C_{3-5}$ alkenyl, aryl or aralkyl;

$R_4$ represents hydrogen, $C_{1-7}$ alkyl, $C_{3-5}$ alkenyl or aralkyl;

n is 2 or 3;

the free valence is attached to either fused ring, and the azabicyclic ring is in either the exo or endo configuration; and acid addition salts and quaternary ammonium salts thereof.

In the compounds of formula (I) $R_1$ and $R_2$ may, for example, independently represent hydrogen, halogen or $C_{1-4}$ alkyl, $R_3$ may be, for example, hydrogen or $C_{1-4}$ alkyl and $R_4$ may be, for example, hydrogen, $C_{1-7}$ alkyl or aralkyl. The carbonyl group is preferably attached to the 3-position of the indole ring. The azabicyclic ring is preferably in the endo configuration.

Another preferred group of compounds for use according to the invention, described in U.K. Specification No. 2100259, may be represented by the general formula (II):

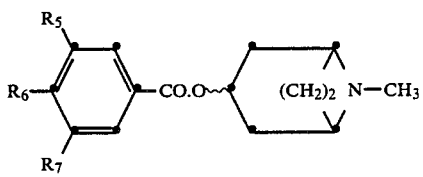

wherein $R_5$ represents $C_{1-4}$ alkyl, $C_{1-4}$ alkoxy, or halogen; and $R_6$ and $R_7$ independently represent hydrogen, $C_{1-4}$ alkyl, $C_{1-4}$ alkoxy or halogen provided that $R_6$ is hydrogen when $R_7$ is hydrogen; and pharmaceutically acceptable salts thereof.

A preferred class of compounds of formula (II) are those in which $R_5$ and $R_7$ are the same and each represents methyl, methoxy or chlorine, and $R_6$ represents hydrogen.

Yet another preferred group of compounds for use according to the invention, described in European Specification No. 200444, may be represented by the general formula (III):

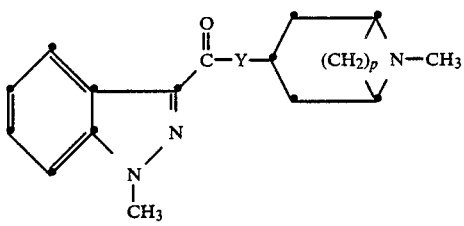

wherein Y is NH or O; and p is 2 or 3; and pharmaceutically acceptable salts thereof.

A further preferred group of compounds for use according to the invention, described in U.K. Patent Specification No. 2153821 and European Specifications Nos. 191562, 210840 and 219193, may be represented by the general formula (IV):

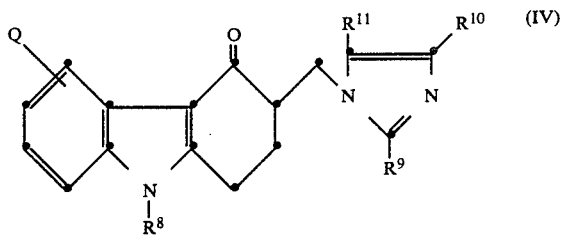

wherein $R^8$ represents a hydrogen atom or a group selected from $C_{1-10}$alkyl, $C_{3-6}$ alkenyl, $C_{3-10}$ alkynyl, $C_{3-7}$cycloalkyl, $C_{3-7}$cycloalkyl $C_{1-4}$alkyl, phenyl or phenyl $C_{1-3}$alkyl, and in the case where Q represents a hydrogen atom, $R^8$ may also represent $-CO_2R^{12}$, $-COR^{12}$, $-CONR^{12}R^{13}$ or $-SO_2R^{12}$ (wherein $R^{12}$ and $R^{13}$, which may be the same or different, each represents a hydrogen atom, a $C_{1-6}$ alkyl or $C_{3-7}$cycloalkyl group, or a phenyl or phenyl$C_{1-4}$alkyl group, in which the phenyl group is optionally substituted by one or more $C_{1-4}$alkyl, $C_{1-4}$alkoxy or hydroxy groups or halogen atoms, with the proviso that $R^{12}$ does not represent a hydrogen atom when $R^8$ represents a group $-CO_2R^{12}$ or $-SO_2R^{12}$); one of the groups represented by $R^9$, $R^{10}$ and $R^{11}$ is a hydrogen atom or a $C_{1-6}$ alkyl, $C_{3-7}$ cycloalkyl, $C_{2-6}$ alkenyl, or phenyl$C_{1-3}$alkyl group, and each of the other two groups, which may be the same or different, represents a hydrogen atom or a $C_{1-6}$ alkyl group; Q represents a hydrogen atom or a halogen atom or a hydroxy, $C_{1-4}$alkoxy, phenyl$C_{1-3}$alkoxy or $C_{1-6}$ alkyl group or a group $-NR^{14}R^{15}$ or $-CONR^{14}R^{15}$ (wherein $R^{14}$ and $R^{15}$, which may be the same or different, each represents a hydrogen atom or a $C_{1-4}$ alkyl or $C_{3-4}$ alkenyl group, or together with the nitrogen atom to which they are attached form a saturated 5 to 7 membered ring); and physiologically acceptable salts and solvates thereof.

A preferred class of compounds represented by the formula (IV) for use according to the present invention is that wherein $R^8$ represents a hydrogen atom or a methyl, ethyl, propyl, prop-2-yl, prop-2-enyl or cyclopentyl group; $R^{10}$ represents a hydrogen atom; and either $R^9$ represents a methyl, ethyl, propyl or prop-2-yl group and $R^{11}$ represents a hydrogen atom or $R^9$ represents a hydrogen atom and $R^{11}$ represents a methyl or ethyl group; and Q represents a hydrogen atom.

A still further preferred group of compounds for use according to the invention, described in European Patent Specification No. 242973, may be represented by the general formula (V):

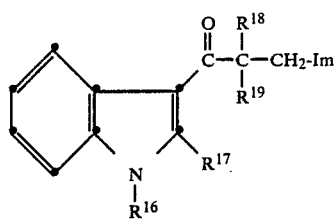

wherein Im represents an imidazolyl group of formula:

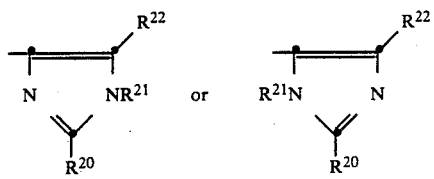

$R^{16}$ represents a hydrogen atom or a $C_{1-6}$ alkyl, $C_{3-6}$ alkenyl, $C_{3-10}$alkynyl, $C_{3-7}$ cycloalkyl, $C_{3-7}$ cycloalkyl$C_{1-4}$alkyl, phenyl or phenyl$C_{1-3}$alkyl group; $R^{17}$ represents a hydrogen atom or a $C_{1-6}$ alkyl, $C_{3-6}$ alkenyl, $C_{3-7}$cycloalkyl, phenyl or phenyl$C_{1-3}$alkyl group; $R^{18}$ and $R^{19}$, which may be the same or different, each represents a hydrogen atom or a $C_{1-6}$ alkyl group; one of the groups represented by $R^{20}$, $R^{21}$ and $R^{22}$, is a hydrogen atom or a $C_{1-6}$ alkyl, $C_{3-7}$ cycloalkyl, $C_{3-6}$ alkenyl, phenyl or phenyl$C_{1-3}$alkyl group, and each of the other two groups, which may be the same or different, represents a hydrogen atom or a $C_{1-6}$ alkyl group; and physiologically acceptable salts and solvates thereof.

A preferred class of compounds represented by the formula (V) for use according to the present invention are those wherein $R^{16}$ represents a hydrogen atom or a methyl, prop-2-enyl or cyclopentyl group; $R^{17}$ represents a hydrogen atom or a methyl group; $R^{18}$ and $R^{19}$ each independently represent a hydrogen atom or a methyl group; $R^{20}$ and $R^{21}$ each represent a hydrogen atom; and $R^{22}$ represents a hydrogen atom or a $C_{1-3}$ alkyl group, most preferably methyl.

Another preferred group of compounds for use according to the invention, described in European Specification No. 235878 and Australian Specification No. 87/67121, may be represented by the general formulae (VI) and (VII) respectively:

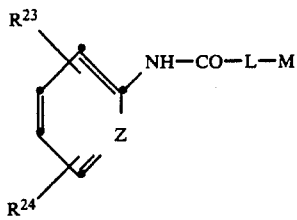

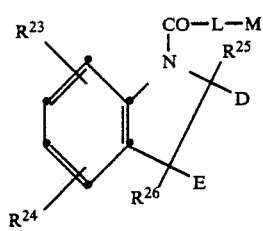

wherein
L is NH or 0;
$R^{23}$ and $R^{24}$ are independently selected from hydrogen, halogen, $CF_3$, $C_{1-6}$alkyl, $C_{1-6}$ alkoxy, $C_{1-6}$alkylthio, $C_{1-7}$acyl, $C_{1-7}$acylamino, $C_{1-6}$alkylsulphonylamino, N-($C_{1-6}$ alkylsulphonyl)-N-$C_{1-4}$alkylamino, $C_{1-6}$alkylsulphinyl, hydroxy, nitro or amino, aminocarbonyl, aminosulphonyl, aminosulphonylamino or N-(aminosulphonyl)-$C_{1-4}$ alkylamino optionally N-substituted by one or two groups selected from $C_{1-6}$alkyl, $C_{3-8}$ cycloalkyl, $C_{3-8}$ cycloalkyl$C_{1-4}$ alkyl, phenyl or phenyl$C_{1-4}$ alkyl groups or optionally N-disubstituted by $C_{4-5}$polymethylene;

Z is a moiety capable of hydrogen bonding to the NH group depicted in formula (VI);

D and E are independently selected from hydrogen or $C_{1-4}$alkyl, or together are a bond;

$R^{25}$ and $R^{26}$ are independently selected from hydrogen, $C_{1-6}$ alkyl, $C_{2-6}$alkenyl$C_{1-4}$alkyl, or together are $C_{2-4}$polymethylene;

M is a group of formula (a), (b) or (c):

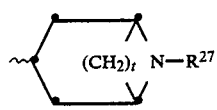

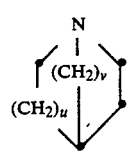

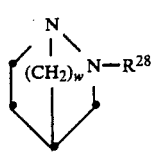

wherein t is 2 or 3; u is 1 or 2; v is 1 to 3; w is 1 to 3; and $R^{27}$ or $R^{28}$ is $C_{1-7}$alkyl, $C_{3-8}$cycloalkyl, $C_{3-8}$cycloalkyl$C_{1-2}$alkyl or $C_{2-7}$alkenyl$C_{1-4}$alkenyl;

and pharmaceutically acceptable salts thereof.

Preferably L is NH; $R^{23}$ is often hydrogen and $R^{24}$ is hydrogen or a 4-substituent such as halogen or methoxy; Z is preferably $C-OCH_3$, $C-OC_2H_5$, $C-OC_3H_7$, $C-CO_2CH_3$, $C-CO_2C_2H_5$ or $SO_2N(CH_3)_2$; often D and E are both hydrogen; often $R^{25}$ and $R^{26}$ are both hydrogen; preferably t is 2 or 3 and u, v and w are 1 or 2; and $R^{27}/R^{28}$ is preferably methyl or ethyl, most preferably methyl.

Yet another preferred group of compounds for use according to the invention, described in U.K. Specification No. 2152049, may be represented by the general formula (VIII):

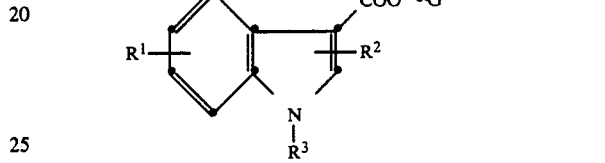

wherein $R^1$, $R^2$ and $R^3$ are as defined for general formula (I) and G is a group of formula (d) or (e):

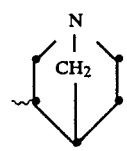

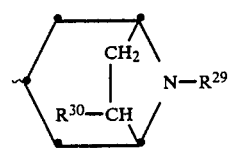

wherein $R^{29}$ is $C_{1-4}$ alkyl and $R^{30}$ is methoxy; and pharmaceutically acceptable salts thereof.

Particularly preferred compounds for use according to the present invention are (3α-tropanyl)-1H-indole-3-carboxylic acid ester and endo-N-(9-methyl-9-azabicyclo[3,3,1]non-3-yl)-1-methylindazole-3-carboxamide and physiologically acceptable salts and solvates thereof.

Other preferred compounds for use according to the present invention are:

3-(5-methyl-1H-imidazol-4-yl)-1-(1-methyl-1H-indol-3-yl)-1-propanone;

1αH, 3α,5αH-tropan-3-yl-3,5-dimethylbenzoate; and physiologically acceptable salts and solvates thereof.

Further preferred compounds for use according to the present invention are:

1αH,3α,5αH-tropan-3-yl-3,5-dichlorobenzoate; indole-[5-(2-methyl-2-azabicyclo(2.2.2)octyl]-3-carboxylate;

1H-indol-3-yl-carboxylic acid (3R*,4S*)-1-azabicyclo-[2.2.1]hept-3-yl ester;

1H-indolyl-3-carboxylic acid 2S-(1-methyl-2-pyrrolidinylmethyl) ester;

4-amino-5-chloro-2-methoxy-N-(3-quinuclidinylmethyl)benzamide;

1-methyl-3-indazolecarboxylic acid (endo-8-methyl-8-azabicyclo [3,2,1]oct-3-yl)ester;
(±)4-amino-5-chloro-2-methoxy-N-(6'α-[4'-thia-1'-azabicyclo[3,3,1]nonyl])benzamide;
(±)4-amino-5-chloro-2-methoxy-N-(6'α-[4'-oxa-1'-azabicyclo[3,3,1]nonyl])benzamide; and physiologically acceptable salts and solvates thereof.

The invention also provides a pharmaceutical composition which comprises an effective amount of at least one compound selected from compounds of formulae (I) to (VIII), for use in medicine, particularly human medicine, for the treatment of dementia and other cognitive disorders.

In a further aspect the invention provides for the use of a compound selected from compounds of formulae (I) to (VIII) for the manufacture of a medicament for the treatment of dementia and other cognitive disorders.

Pharmaceutical compositions for use according to the present invention may be formulated in conventional manner, optionally with one or more physiologically acceptable carriers and/or excipients. For example, the compounds described in the aforementioned patent specifications may be formulated in the manner described therein.

Compounds for use according to the present invention may be formulated for oral, buccal, parenteral, rectal or transdermal administration or in a form suitable for administration by inhalation or insufflation (either through the mouth or the nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

Compounds for use according to the present invention may be formulated for parenteral administration by injection e.g. by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds for use according to the present invention may also be formulated in rectal compositions such as suppositories or retention enemas, e.g. containing conventional suppository bases such as cocoa butter or other glycerides.

In addition to the formulations described previously, the compounds may also be formulated as a depot preparation. Such long acting formulations may be administered by implantation (for example subcutaneously, transcutaneously or intramuscularly) or by intramuscular injection. Thus, for example, the compounds for use according to the present invention may be formulated with suitable polymeric or hydrophobic materials (for example as an emulsion in an acceptable oil) or ion exchange resins, or as sparingly soluble derivatives, for example, as a sparingly soluble salt.

The dose at which the compounds may be administered to man will depend upon the route of administration, the body weight of the patient, the severity of the condition to be treated and the potency of the compounds. For example, the compounds disclosed in the aforementioned patent specifications may be administered at doses in the ranges specified therein for the compounds, or at lower doses for example 0.5 μg to 20 20 mg e.g. 0.005–20 mg, preferably 0.05–10 mg per unit dose which may be administered, for example, 1 to 4 times per day.

Thus a unit dose of a compound of formula (I) as herein defined may contain from 0.2 to 250 mg of the active ingredient, and may be administered for example up to four times per day, such that the overall daily dose is in the range 0.5 to 500 mg.

A unit dose of a compound of formula (II) as herein defined may contain from about 0.5 to 100 mg of the active ingredient, usually 1 to 50 mg and preferably 3 to 30 mg, and may be administered, for example, from 1 to 4 times per day.

A unit dose of a compound of formula (III) as herein defined may contain 0.5 to 1000 mg of the active ingredient, for example 1 to 500 mg, and may be administered, for example, 1 to 4 times per day, such that the total daily dose is in the range 0.001 to 50 mg/kg, more usually 0.002 to 25 mg/kg.

A unit dose of a compound of formula (IV) as herein defined may contain 0.05 to 20 mg of the active ingredient, preferably 0.1 to 10 mg, and may be administered 1 to 4 times per day.

A unit dose of a compound of formula (V) as herein defined may contain 0.001 to 100 mg of the active ingredient, preferably 0.01 to 50 mg, and may be administered 1 to 4 times per day.

A unit dose of a compound of formula (VI) as herein defined may contain 0.05 to 1000 mg of the active ingredient, for example 0.1 to 500 mg, and may be administered, for example, 1 to 4 times per day, such that the total daily dose is in the range 0.0001 to 50 mg/kg, more usually 0.0002 to 25 mg/kg.

A unit dose of a compound of formula (VII) as herein defined may contain 0.05 to 1000 mg of the active ingredient, for example 0.5 to 500 mg, and may be administered, for example, 1 to 4 times per day, such that the total daily dose is in the range 0.0001 to 50 mg/kg, more usually 0.0002 to 25 mg/kg.

A unit dose of a compound of formula (VIII) as herein defined may contain from 0.1 to 250 mg of the active ingredient, and may be administered up to four times per day, such that the overall daily dose is in the range 0.5 to 500 mg.

The following examples illustrate pharmaceutical formulations for use according to the invention, containing either (3α-tropanyl)-1H-indole-3-carboxylic acid ester or 3-(5-methyl-1H-imidazol-4-yl)-1-(1-methyl-1H-indol -3-yl)-1-propane as the active ingredient. Other compounds for use according to the invention may be formulated in a similar manner.

TABLETS FOR ORAL ADMINISTRATION

Tablets may be prepared by the normal methods such as direct compression or wet granulation.

The tablets may be film coated with suitable film forming materials, such as hyroxypropyl methylcellulose, using standard techniques. Alternatively the tablets may be sugar coated.

| Direct Compression Tablet | |
|---|---|
|  | mg/tablet |
| Active Ingredient | 0.50 |
| Calcium Hydrogen Phosphate BP* | 87.25 |
| Croscarmellose Sodium NF | 1.8 |
| Magnesium Stearate BP | 0.45 |
| Compression weight | 90.0 |

*of a grade suitable for direct compression.

The active ingredient is passed through a 60 mesh sieve, blended with the calcium hydrogen phosphate, croscarmellose sodium and magnesium stearate. The resultant mix is compressed into tablets using a Manesty F3 tablet machine fitted with 5.5 mm, flat bevelled edge punches.

Tablets of other strengths may be prepared by altering the ratio of active ingredient to excipients or the compression weight and using punches to suit.

| CAPSULES | |
|---|---|
|  | mg/capsule |
| Active Ingredient | 0.5 |
| *Starch 1500 | 98.5 |
| Magnesium Stearate BP | 1.0 |
| Fill Weight | 100.0 |

*a form of directly compressible starch.

The active ingredient is sieved and blended with the excipients. The mix is filled into size No. 2 hard gelatin capsules using suitable machinery. Other doses may be prepared by altering the fill weight and if necessary changing the capsule size to suit.

| SYRUP | |
|---|---|
| This may be either a sucrose or sucrose free presentation. | |
| Sucrose-Free | mg/5 ml dose |
| Active ingredient | 0.5 |
| Hydroxypropylmethylcellulose USP (viscosity type 4000) | 22.5 |
| Buffer | |
| Flavour | |
| Colour | as required |
| Preservative | |
| Sweetener | |

| -continued | |
|---|---|
| SYRUP | |
| This may be either a sucrose or sucrose free presentation. | |
| Sucrose-Free | mg/5 ml dose |
| Purified Water BP to | 5.0 ml |

The hydroxypropylmethylcellulose is dispersed in hot water, cooled and then mixed with an aqueous solution containing the active ingredient and the other components of the formulation. The resultant solution is adjusted to volume and mixed. The syrup is clarified by filtration.

| INJECTION FOR INTRAVENOUS ADMINISTRATION | | |
|---|---|---|
|  | mg/ml | |
| Active ingredient | 0.05 | 0.5 |
| Sodium Chloride BP | as required | as required |
| Water for Injection BP to | 1.0 ml | 1.0 ml |

Sodium chloride may be added to adjust the tonicity of the solution and the pH may be adjusted, using acid or alkali, to that of optimum stability and/or facilitate solution of the active ingredient. Alternatively suitable buffer salts may be used.

The solution is prepared, clarified and filled into appropriate size ampoules sealed by fusion of the glass. The injection is sterilised by heating in an autoclave using one of the acceptable cycles. Alternatively the solution may be sterilised by filtration and filled into sterile ampoules under aseptic conditions. The solution may be packed under an inert atmosphere of nitrogen or other suitable gas.

| SUPPOSITORY | |
|---|---|
| Active Ingredient | 0.5 mg |
| *Witeosol H15 to | 1.0 g |

*Witepsol H15 is a proprietary grade of Adeps Solidus Ph. Eur.

A suspension of the active ingredient is prepared in the molten Witepsol and filled, using suitable machinery, into 1 g size suppository moulds.

The efficacy of the compounds for use according to the invention in the treatment of cognitive disorders has been demonstrated in marmosets given learning tasks in the Wisconsin General Test Apparatus.

Test compounds: (3α-Tropanyl)-1H-indole-3-carboxylic acid ester and 3-(5-methyl-1H-imidazol-4-yl)-1-(1-methyl-1H-indol-3-yl)-1-propanone.

Marmoset learning tasks in the Wisconsin General Test Apparatus

Introduction and Test Procedure

Common marmosets were tested for performance in a discriminative learning task and reverse learning task using the Wisconsin General Test apparatus described by Harlow H. F., Psychological Review, 56, 51–65, 1949. The experiments were essentially carried out following the experimental protocol of Baker H. F., Ridley R. M. and Drewett, B., Psychopharmacology, 91, 512–514, 1987. The test compound was administered into the hind leg of the marmoset as a subcutaneous (s.c) injection in 1 ml of saline.

Results

Administration of either of the test compounds at a dose of 10 ng/kg s.c. twice a day throughout testing improved the performance of the marmosets in the reverse learning task.

I claim:

1. A method for the treatment of dementia and other cognitive disorders which comprises administering to a human or animal subject suffering from dementia or another cognitive disorder an effective amount for the treatment of said dementia or other cognitive disorder of a compound of formula I

TABLE I

| Design Parameters for a Narrow-Band Optical Interference Filter of the 1.0 HL HH LHLHL HH L'H 1.0 Type | | |
|---|---|---|
| | Optical Thin Film Filter (Pass Wavelength = 1.00 um) | |
| | Refractive Index | Thickness (A) |
| Input Region | 1.00 | ... |
| Region 1 (H) | 4.00 | 625.000 |
| Region 2 (L) | 1.35 | 1851.852 |
| Region 3 (L') | 1.83 | 1366.120 |
| Output Region | 1.00 | ... | wherein $R_1$ and $R_2$ independently represent hydrogen, halogen, $C_{1-4}$ alkyl, $C_{1-4}$ alkoxy, hydroxy, amino, $C_{1-4}$ alkylamino, di($C_{1-4}$)alkylamino, mercapto or $C_{1-4}$ alkylthio;

$R_3$ represents hydrogen, $C_{1-4}$ alkyl, $C_{3-5}$ alkenyl, aryl or aralkyl;

$R_4$ represents hydrogen, $C_{1-7}$ alkyl, $C_{3-5}$ alkenyl or aralkyl;

n is 2 or 3;

the free valence is attached to either fused ring, and the azabicyclic ring is in either the exo or endo configuration; or a physiologically acceptable salt or solvate thereof.

2. A method according to Claim 1 wherein $R_1$ and $R_2$ independently represent hydrogen, halogen or $C_{1-4}$ alkyl; $R_3$ represents hydrogen or $C_{1-4}$ alkyl; $R_4$ represents hydrogen, $C_{1-7}$ alkyl or aralkyl; the carbonyl group is attached to the 3-position of the indole ring, and the azabicyclic ring is in the endo configuration.

3. A method according to claim 1 wherein said compound selected from compounds of formula (I) is administered in a dose of 0.5 μg to 20 mg from 1 to 4 times per day.

4. A method according to claim 1 wherein said compound selected from compounds of formula (I) is administered in a dose of 0.05 mg to 10 mg from 1 to 4 times per day.

5. A method for the treatment of dementia and other cognitive disorders which comprises administering to a human or animal subject suffering from dementia or another cognitive disorder an effective amount for the treatment of said dementia or other cognitive disorder of -(3α-tropanyl)-1H-indole-3-carboxylic acid ester or a physiologically acceptable salt or solvate thereof.

* * * * *

UNITED STATES PATENT AND TRADEMARK OFFICE
CERTIFICATE OF CORRECTION

PATENT NO. : 4,985,437

DATED : January 15, 1991

INVENTOR(S) : Michael B. TYERS

It is certified that error appears in the above-identified patent and that said Letters Patent is hereby corrected as shown below:

Claim 1, beginning at line 14, delete

"
| TABLE I | | |
|---|---|---|
| Design Parameters for a Narrow-Band Optical Interference Filter of the 1.0 HL HH LHLHL HH L'H 1.0 Type | | |
| | Optical Thin Film Filter (Pass Wavelength = 1.00 um) | |
| | Refractive Index | Thickness (A) |
| Input Region | 1.00 | ... |
| Region 1 (H) | 4.00 | 625.000 |
| Region 2 (L) | 1.35 | 1851.852 |
| Region 3 (L') | 1.83 | 1366.120 |
| Output Region | 1.00 | ... |
"

UNITED STATES PATENT AND TRADEMARK OFFICE
CERTIFICATE OF CORRECTION

PATENT NO. : 4,985,437

DATED : January 15, 1991

INVENTOR(S) : Michael B. Tyers

It is certified that error appears in the above-identified patent and that said Letters Patent is hereby corrected as shown below:

and insert --

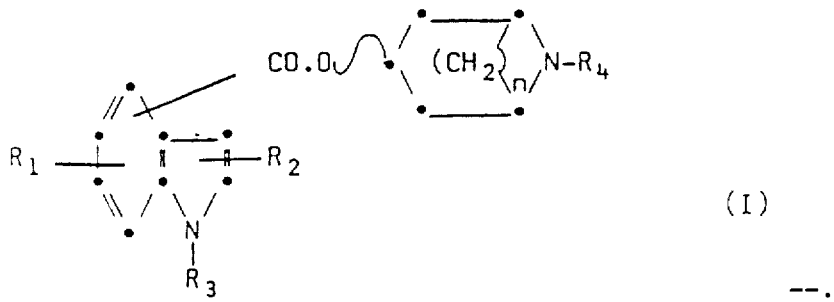

(I)

--.

Signed and Sealed this

Twenty-eighth Day of July, 1992

Attest:

DOUGLAS B. COMER

Attesting Officer      Acting Commissioner of Patents and Trademarks